United States Patent [19]
O'Regan

[11] Patent Number: 5,741,273
[45] Date of Patent: Apr. 21, 1998

[54] ELASTIC BAND LIGATION DEVICE FOR TREATMENT OF HEMORRHOIDS

[76] Inventor: Patrick J. O'Regan, 912-750 West Broadway, Vancouver, B.C., Canada, V5Z 1H2

[21] Appl. No.: 614,074

[22] Filed: Mar. 8, 1996

[51] Int. Cl.⁶ ............................ A61M 1/00; A61B 17/22
[52] U.S. Cl. .................................. 606/140; 606/1
[58] Field of Search .................. 606/1, 110–115, 606/139–142, 144, 145–148, 151, 228; 604/902

[56] References Cited

U.S. PATENT DOCUMENTS

| | | | |
|---|---|---|---|
| 3,760,810 | 9/1973 | Van Hoorn | 606/140 X |
| 4,257,419 | 3/1981 | Goltner et al. | 606/140 |
| 5,122,149 | 6/1992 | Broome | 606/140 |
| 5,158,563 | 10/1992 | Cosman | 606/140 |
| 5,203,863 | 4/1993 | Bidoia | 606/140 |
| 5,269,789 | 12/1993 | Chin et al. | 606/140 |
| 5,320,630 | 6/1994 | Ahmed | 606/140 |
| 5,398,844 | 3/1995 | Zaslavsky et al. | 221/208 |
| 5,423,834 | 6/1995 | Ahmed | 606/140 |
| 5,462,559 | 10/1995 | Ahmed | 606/140 |
| 5,464,412 | 11/1995 | Budding | 606/140 |

OTHER PUBLICATIONS

New Device For Rubber Band Ligation of Hemorrhoids Fabio Gat et al, Journal: Dis Colon Rectum Published 1994 vol. 37 No. 5 pp. 494–495.

Office Ligation Treatment of Hemorrhoids James Baron, Journal: Diseases of Colon & Rectum Published May 3, 1962 vol. 6 pp. 109–113.

Elastic Band Ligation of Haemorrhoids: A New Applicator P.F. Schofield et al Journal: Brit. J. Surgery Published Mar. 1984 vol. 73 No. 3 p. 212.

The One–Man Bander: A New Instrument For Elastic Ligation of Piles. Hamish Thomson Journal: The Lancet Published Nov. 8, 1980 p. 1006.

*Primary Examiner*—Michael Buiz
*Assistant Examiner*—Nancy Connolly Mulcare
*Attorney, Agent, or Firm*—Graham & James LLP

[57] ABSTRACT

An elastic band ligation device for treatment of hemorrhoids permits a doctor to band hemorrhoidal tissue without an assistant and does not have to be attached to an aspirator. The device has the capability of suctioning tissue into a tubular member before banding. A plastic inner tubular member retains a stretched elastic band over a front end of an inner tubular member which extends for a sufficient length for insertion into the rectum of a patient. A plunger in the tubular member may be slid backwards to draw a suction in the tubular member to draw tissue in through the front end. A plastic outer pusher sleeve fits over the tubular member and is adapted to push the elastic band off the front end of the tubular member to capture the hemorrhoidal tissue drawn into the tubular member.

13 Claims, 1 Drawing Sheet

ELASTIC BAND LIGATION DEVICE FOR TREATMENT OF HEMORRHOIDS

TECHNICAL FIELD

The present invention relates to the treatment of hemorrhoids by elastic band ligation, sometimes referred to as rubber band ligation, and more specifically to an elastic band ligation device that may be used by a single operator.

BACKGROUND ART

The treatment of hemorrhoids by elastic band ligation is credited to Blaisdell who described this technique in Diseases of the Colon and Rectum in 1963. The technique involves placing an elastic band on tissue in the rectum above the area of the hemorrhoid where there is little sensation. The tissue trapped in the band being cut off from its blood supply degenerates and is sloughed, and the elastic band along with the sloughed tissue is passed with the bowel motions. More importantly, however, the resulting healing process causes the tissue in the vicinity to become fixed and prolapse of the hemorrhoidal tissue is minimized. Furthermore, the elastic band ligation technique has been found to give relief of hemorrhoidal symptoms.

Many devices exist on the market today utilizing the elastic band ligation technique. Examples are U.S. Pat. No. 5,203,863 to Bidoia, U.S. Pat. No. 5,122,149 to Broome and U.S. Pat. No. 5,158,563 to Cosman. The devices disclosed in these patents are generally designed to be used in conjunction with an instrument such as a proctoscope or anoscope to directly see the area to be banded. In some cases it is necessary to have an assistant to hold the proctoscope or anoscope and the use of these scopes, which are generally larger in diameter than the banding apparatus, can cause considerable discomfort to a patient and more specifically to one who is suffering symptoms of hemorrhoids.

It is an aim of the present invention to provide an elastic band ligation device for treatment of hemorrhoids that may be used without directly seeing the site for banding. Thus, it may be used without a proctoscope or anoscope or any other type of scope or viewing technique. Therefore, because the device can be inserted into the rectum and positioned appropriately without simultaneous visualization, or the need for any type of scope, the banding procedure performed in this manner causes less discomfort to the patient.

In many patients such as in those of small size or in those who have a degree of anal stenosis or fibrosis, examination and banding through the proctoscope or anoscope may be difficult or impossible because of the required large diameter of the scope.

On the other hand, in patients who are large in size or in those who are obese it may be difficult or impossible to reach and expose the area for banding with an appropriate proctoscope or anoscope.

The above conditions generally do not pose difficulties in banding hemorrhoids with the device of the present invention, and many patients who might otherwise require costly hospitalization and painful hemorrhoidectomy can be treated by this technique.

Furthermore, it is an aim of the present invention to provide an elastic band ligation device that has a suction device incorporated therein to draw hemorrhoidal tissue into an aperture for banding without requiring a second operator or connection to an aspirator.

Ligation may be performed by initially inspecting the site through a small scope such as a sigmoidoscope, anoscope, proctoscope or other type of scope and making a mental note as to the area where the band should optimally be placed. The scope is then removed and the ligation device is placed in the rectum. At first the front end of the device is inserted well past the site for banding. Then the device is gently withdrawn while it is angled acutely to point in the direction of the site. As the device is being withdrawn, marks on its surface appear on the anal verge which can be used as a guide to the level where the band should optimally be placed in the rectum. Thus the band can be placed accurately both with regards to the depth inside the rectum as well as its circumference. The band can then be placed satisfactorily without requiring the use of a second instrument to see the placement. This means that only a single operator is required, first of all, to inspect the hemorrhoidal tissue through a scope, and then to band the tissue. With regard to the accuracy of the location of the banding, it has been found that even when bands are placed by direct viewing, re-examination often reveals that the band may be as much as 45 degrees off in one direction or another as far as the circumference of the rectum is concerned. The aiming and measuring steps necessary to band the hemorrhoidal tissues without viewing at the same time has been found to be reasonably accurate.

DISCLOSURE OF INVENTION

A single operator elastic band ligation device is provided that is self contained having all the necessary elements to complete the ligation of internal hemorrhoidal tissue, including the capability of suctioning the hemorrhoidal tissue into a cylinder, and the placing of an elastic band around the tissue. The elastic band is expanded and positioned around the front end of an inner tubular member. The band is discharged by advancing an outer sleeve over the inner tubular member and thus placing the elastic band over the hemorrhoidal tissue sucked into the inner tubular member.

In one embodiment, the ligation device is disposable after use.

The present invention provides a single operator elastic band ligation device for treatment of hemorrhoidal tissue comprising a plastic inner tubular member for retaining a stretched elastic band over a front end, the inner tubular member extending for a sufficient length for insertion into the rectum of a patient, and having a plunger in the tubular member with a handle means extending away from the front end, the handle means for sliding the plunger away from the front end of the inner tubular member to provide a suction for drawing hemorrhoidal tissue into the inner tubular member through an opening at the front end, and a plastic outer tubular pusher sleeve fitting and having a limited friction fit over the inner tubular member, with an external end of the outer tubular sleeve adjacent the stretched elastic band, and having an opposite end of the outer tubular pusher sleeve with thumb push means for an operator to push the outer tubular pusher sleeve towards the front end of the inner tubular member and release the elastic band from the front end of the inner tubular member to engage hemorrhoidal tissue through the opening in the inner tubular member.

The disposable elastic band ligation device may be used in a doctor's office and does not generally require any form of anaesthetic. One to three bands are generally placed at each patient visit and as many as six bands may be required in total, particularly in advanced cases. In one embodiment the ligation device is made of plastic and is disposable, therefore, once it has been used it is discarded and does not have to be sterilized. In another embodiment, the ligation device is made of metal and may be sterilized after each use.

BRIEF DESCRIPTION OF DRAWINGS

In drawings which illustrate embodiments of the present invention.

BEST MODE FOR CARRYING OUT THE INVENTION

Figure 1:
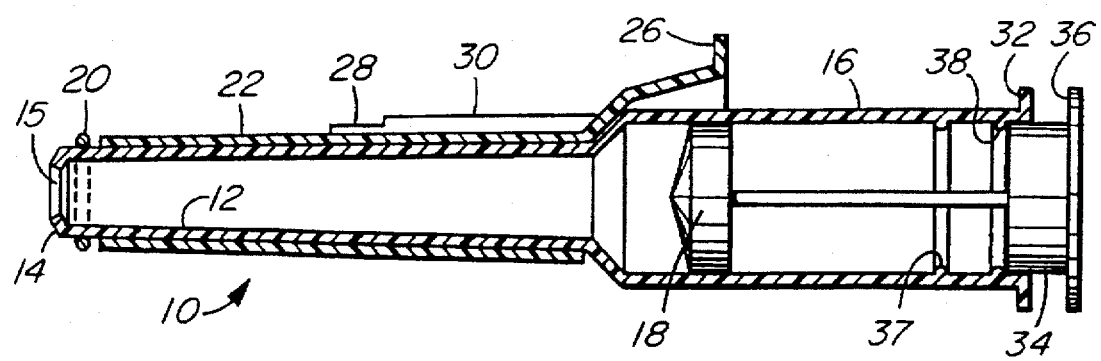
FIG. 1 is a sectional elevational view showing an elastic band ligation device according to one embodiment of the present invention.

In one embodiment, the elastic band ligation device of the present invention is made out of plastic, either clear or opaque plastic, and is disposable. In another embodiment, the ligation device is made from stainless steel and may be sterilized after each use. As shown in FIG. 1, the ligation device 10 has an inner tubular member 12 with a rounded, bevelled or radiused front end 14 which has an opening 15 slightly smaller in diameter than the inner tubular member 12. The inner tubular member 12 may be slightly tapered increasing in diameter as it extends back from the front end 14. In another embodiment the inner tubular member 12 may be cylindrical in shape with no taper. The length of the inner tubular member 12 is sufficient for insertion into the rectum of a patient for treatment of hemorrhoidal tissue. The inner tubular member 12 is integral with a plunger housing 16 which has a plunger 18 therein, thus when the plunger 18 is moved back in the plunger housing 16, a suction occurs at the opening 15 of the front end 14. In another embodiment, the plunger housing 16 and inner tubular member 12 may be separate components joined together.

A stretched elastic band 20, or rubber band as referred to in some cases, is positioned over the inner tubular member 12 adjacent the front end 14. An outer tubular pusher sleeve 22 fits over the inner tubular member 12 and has a limited friction fit on the inner tubular member 12. When the outer tubular pusher sleeve 22 is pushed forwards toward the front end 14 of the inner tubular member 12, the elastic band is pushed off the front end 14 of the inner tubular member 12 and engages hemorrhoidal tissue which has been sucked into the opening 15 in the front end of the inner tubular member 12.

Figure 2:
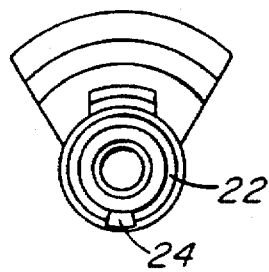
FIG. 2 is an end view showing the ligation device of FIG. 1.

The outer tubular pusher sleeve 22 is shown having a longitudinal slit 24 as shown in FIG. 2 so the sleeve is in effect a clip around the inner tubular member 12. In another embodiment, the pusher sleeve 22 is tubular and slides over the inner tubular member 12. On one side of the outer tubular pusher sleeve 22 is a partial pusher flange 26 extending from the end of the pusher sleeve 22. The pusher flange 26 allows the pusher sleeve 22 to be pushed by a thumb of an operator so the elastic band 20 is discharged from the front end 14 of the inner tubular member 12. A first raised step 28 and a second raised step 30 are shown on one side of the pusher sleeve 22 adjacent the pusher flange 26. These steps are markets provided for an operator to position the ligation device 10 either by sight or by feel. In one embodiment, longitudinal ribs (not shown) are provided on the inside of the pusher sleeve 22 for friction purposes to ensure the pusher sleeve does not slide freely on the inner tubular member 12 and only moves when pushed by an operator.

The plunger housing 16 is substantially cylindrical and is not tapered and an outside shoulder 32 allows the housing 16 to be gripped when the plunger 18 is pulled back. The plunger 18 is attached to a stem 34 having a cross-section as shown in FIG. 1, with a shoulder 36 to act as a grip so that the plunger 18 can be pulled out of the housing 16 to draw suction through the opening 15 in the front end 14 of the inner tubular member 12.

A first shoulder ring 37 is located towards the end of the housing 16 and acts as a locking system so that when the plunger 18 is pulled back and rides over the first shoulder ring 37 it is held in that position and holds a vacuum in the housing 16 and the inner tubular member 12. If there was no locking system, the plunger 18 would immediately return to the original position and no vacuum would remain to pull the hemorrhoidal tissue into the inner tubular member 12. A second shoulder ring 38 is positioned outside the first shoulder ring 37 and acts as a stop to prevent the plunger 18 from being pulled out of the housing 16.

Whereas shoulders 37,38 are shown for locking the plunger 18 in the housing 16, it will be apparent to those skilled in the art that other types of clamping systems to stop the plunger 18 returning in the housing 16 may be provided.

In operation once a doctor has examined the rectum of a patient and discovered the position of the hemorrhoidal tissue, he removes the scope through which the inspection has initially occurred, memorizing the position of the hemorrhoidal tissue and then inserts the ligation device similar to that shown in FIG. 1. The opening 15 at the front end 14 of the inner tubular member 12 is positioned as close as possible to the hemorrhoidal tissue and the operator holds the housing 16, draws back the plunger 18 past the first shoulder ring 37 so a vacuum is formed in the housing 16 and the hemorrhoidal tissue is pulled into the inner tubular member 12 through the opening 15. When this has been accomplished, the doctor releases the shoulder 36 of the plunger 18 and pushes the outer plastic pusher sleeve 22 forward so that the stretched elastic band 20 is pushed off the front end 14 of the inner tubular member 12 to capture the hemorrhoidal tissue. The ligation device can then be removed and the procedure may be carried out at least three times during one patient's visit to the doctor's office. No aspirator or other device need be attached to the ligation device as the built in plunger mechanism sucks the hemorrhoidal tissue into the inner tubular member 12 and holds it there for the doctor to place the elastic bands.

Figure 3:
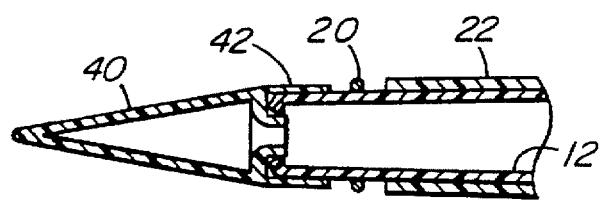
FIG. 3 is a partial sectional elevational view showing a cone shaped loading device for expanding an elastic band as it is loaded onto the ligation device.

A cone shaped loading device 40 is shown in FIG. 3 and has a thin sleeve 42 that overlaps the front end 14 of the inner tubular member 12. An elastic band 20 is pushed over the loading device 40 and expanded as it is moved along until the elastic band 20 is pushed off the sleeve 42 onto the front end 14 of the inner tubular member 12. The loading device 40 is then removed and the elastic band is moved to the position shown in FIG. 1.

The thin sleeve 42 of the loading device 40 prevents the elastic band becoming lodged in the join between the loading device 40 and the inner tubular member 12.

Figure 4:
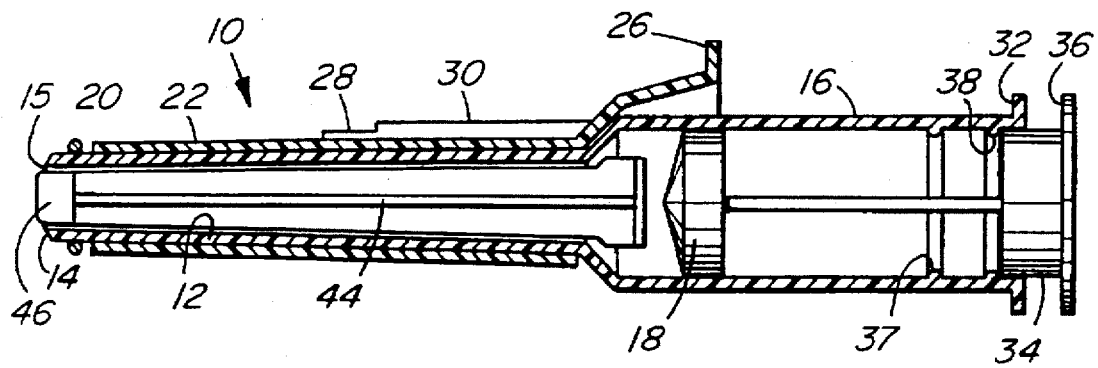
FIG. 4 is a sectional elevational view showing an elastic band ligation device similar to that shown in FIG. 1 including an obturator.
Figure 5:
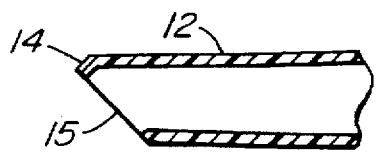
FIG. 5 is a partial elevational view showing a portion of an inner tubular member of an elastic band ligation device with an angled front end.

In another embodiment an obturator 44 is provided which fits inside the inner tubular member 12 as shown in FIG. 4. The obturator 44 has a button shaped front end 46 which protrudes slightly through the opening 15 at the front end 14 of the inner tubular member 12. The purpose of the obturator 44 is to improve access of the ligation device 10 when it is inserted into the rectum. It avoids the edge of the opening 15 at the front end 14 from snagging on hemorrhoidal tissue thus causing discomfort to a patient. The plunger 18 resting and pushing against the outer end of the obturator 44, maintains it in position as the device is being inserted into the rectum. Once the ligation device 10 has been positioned, the doctor draws back the plunger 18 and the obturator 44 moves back with the plunger 18 exposing the opening 15 at the front end 14 of the inner tubular member 12 and hemorrhoidal tissue is pulled into the inner tubular member 12 through the opening 15.

As shown in FIG. 1, the front end 14 of the inner tubular member 12 is rounded or radiused to allow a doctor to insert the ligation device 10 at any angle and not cause snagging or discomfort to a patient. The ligation devices 10 may be made in different sizes. 8 mm, 10 mm and 12 mm inside diameters of the inner tubular member 12 are preferred sizes. The dimension of the opening 15 is generally about 0.5 to 1 mm less than the internal diameter of the inner tubular member to permit radiused rounded edges at the front end 14. The obturator 44 is generally used in the larger ligation devices although may be provided in all sizes.

In another embodiment, shown in FIG. 4, the front end 14 of the inner tubular member is at an angle and not perpendicular to the axis of the inner tubular member 12. This angled front end 14 and opening 12 is for ease of placing the ligation device on the side wall of the rectum to capture hemorrhoidal tissue.

Various changes may be made to the embodiments shown herein without departing from the scope of the present invention which is limited only by the following claims.

The embodiments of the present invention in which an exclusive property or privilege is claimed are defined as follows:

1. A single operator elastic band ligation device for treatment of hemorrhoidal tissue, comprising:
   a plastic inner tubular member for retaining a stretched elastic band over a front end, the inner tubular member extending for a sufficient length for insertion into the rectum of a patient, and having a plunger in the tubular member with a handle means extending away from the front end, the handle means for sliding the plunger away from the front end of the inner tubular member to provide a suction for drawing hemorrhoidal tissue into the inner tubular member through an opening at the front end, and
   a plastic outer tubular pusher sleeve fitting and having a limited friction fit over the inner tubular member, with an insertion end of the outer tubular sleeve adjacent the stretched elastic band, and having an opposite end of the outer tubular pusher sleeve with thumb push means for an operator to push the outer tubular pusher sleeve towards the front end of the inner tubular member and release the elastic band from the front end of the inner tubular member to engage hemorrhoidal tissue through the opening in the inner tubular member.

2. The elastic band ligation device according to claim 1 wherein the inner tubular member and the outer tubular pusher sleeve have a taper with the diameter increasing from the front end.

3. The elastic band ligation device according to claim 1 wherein the inner tubular member includes a plunger housing, spaced from the front end, of the inner tubular member the plunger sliding in the plunger housing to provide a suction therein.

4. The elastic band ligation device according to claim 1 including a cone shaped loader means for insertion into the front end of the inner tubular member for loading said elastic band over the front end of the inner tubular member.

5. The elastic band ligation device according to claim 4 wherein the cone shaped loader has a thin sleeve that overlaps the front end of the inner tubular member.

6. The elastic band ligation device according to claim 1 wherein the outer tubular pusher sleeve has a slot extending parallel to a sleeve axis.

7. The elastic band ligation device according to claim 1 wherein the plastic inner tubular member and the plastic outer tubular pusher sleeve are constructed of stainless steel instead of plastic.

8. The elastic band ligation device according to claim 1 wherein the pusher sleeve has markers thereon to aid in positioning the device in the rectum of a patient.

9. The elastic band ligation device according to claim 1 wherein the front end of the inner tubular member is radiused.

10. The elastic band ligation device according to claim 1 wherein the front end of the inner tubular member is sloped at an angle to an axis of the tubular member.

11. The elastic band ligation device according to claim 1 including locking means to hold the plunger in a pulled back position in the tubular member to retain a suction in the inner tubular member.

12. The elastic band ligation device according to claim 11 wherein the locking means is at least one shoulder ring in the tubular member to prevent the plunger from moving.

13. The elastic band ligation device according to claim 1 including an obturator fitting within the inner tubular member that has a front portion filling the opening at the front end of the inner tubular member, the obturator moving with the plunger when slid away from the front end.

* * * * *